United States Patent
Bonomo et al.

(10) Patent No.: US 8,466,307 B2
(45) Date of Patent: Jun. 18, 2013

(54) RUTHENIUM BASED COMPLEXES

(75) Inventors: Lucia Bonomo, Geneva (CH); Philippe Dupau, Geneva (CH); Serge Bonnaudet, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/641,902

(22) PCT Filed: May 13, 2011

(86) PCT No.: PCT/IB2011/052108
§ 371 (c)(1),
(2), (4) Date: Oct. 18, 2012

(87) PCT Pub. No.: WO2011/145032
PCT Pub. Date: Nov. 24, 2011

(65) Prior Publication Data
US 2013/0035499 A1 Feb. 7, 2013

(30) Foreign Application Priority Data
May 21, 2010 (EP) .................................... 10163504

(51) Int. Cl.
*C07F 15/00* (2006.01)
(52) U.S. Cl.
USPC ........................................... 556/136; 556/21
(58) Field of Classification Search
USPC .................................................. 556/21, 136
See application file for complete search history.

(56) References Cited

PUBLICATIONS

International Search Report and Written Opinion of the International Searching Authority, application No. PCT/IB2011/052108, mailed Feb. 2, 2012.
Albers et al., "Dinuclear Ruthenium (II) Carboxylate Complexes," Inorganic Syntheses, 26:249-258 (Nov. 1989).
Albers et al., "Dimeric ruthenium(II) complexes containing bridging carboxylato and aquo ligands. The crystal structure of μ-aquobis(μ-trifluoroacetato)bis[($\eta^4$-cycloocta-1,5-diene)(trifluoroacetato)ruthenium(II)]," Journal of Organometallic Chemistry, 272(3):C62-C66 (Sep. 1984).
Doucet et al., "Enantioselective Hydrogenation of 2'-Chloroacetophenone with ((R)-Binap)Ru($O_2CAr$)$_2$ complexes : Influence of Carboxylate Ligands and Solvents," Tetrahedron: Asymmetry, 7(2):525-528 (Feb. 1996).
Heiser et al., "New Efficient Methods for the Synthesis and In-Situ Preparation of Ruthenium(II) Complexes of Atropisomeric Diphosphines and Their Application in Asymmetric Catalytic Hydrogenations," Tetrahedron: Asymmetry, 2(1):51-62 (1991).
Kavanagh et al., "Mono- and Bi-dentate Carboxylato Complexes of Ruthenium(IV)," J. Chem. Soc., Dalton Trans., 2:327-335 (1993).
Noyori et al., "Asymmetric Synthesis of Isoquinoline Alkaloids by Homogeneous Catalysis," J. Am. Chem. Soc., 108(22):7117-7119 (Oct. 1986).
Ohta et al., "Asymmetric Hydrogenation of Unsaturated Carboxylic Acids Catalyzed by BINAP-Ruthenium(II) Complexes," J. Org. Chem., 52(14):3174-3176 (Jul. 1987).
Takaya et al., "Enantioselective Hydrogenation of Allylic and Homoallylic Alcohols," J. Am. Chem. Soc., 109(5):1596-1597 (Mar. 1987).

*Primary Examiner* — Porfirio Nazario Gonzalez
(74) *Attorney, Agent, or Firm* — Winston & Strawn LLP

(57) ABSTRACT

The present invention relates to the field of one step process for the preparation of monomeric or dimeric [Ru(diene)(OOCR)$_2$]$_n$ complexes from [(diene)RuCl$_2$]$_n$, as well as a new class of [Ru(diene)(OOCR)$_2$]$_n$ complexes and their use to prepare [Ru(PP)(OOCR)$_2$] complexes, which are good catalysts.

8 Claims, No Drawings

RUTHENIUM BASED COMPLEXES

TECHNICAL FIELD

The present invention relates to the field of catalysis and, more particularly, to the preparation of specific monomeric or dimeric ruthenium complexes, and the use of new monomeric or dimeric ruthenium complexes as useful precursors for a number of known types of catalysts. All of said invention's ruthenium complexes are formally Ru(II) complexes. Some of said specific ruthenium complexes possess a number of important advantages over the similar prior art known precursors.

PRIOR ART

Some ruthenium carboxylates complexes of general formula [Ru(diene)(OOCR)$_2$]$_n$, with n equals 1 or 2, have been described as useful starting compounds for the preparation of a number of Ruthenium-diphosphine (PP) complexes of formula [Ru(PP)(OOCR)$_2$], which are good catalysts, for example, in the hydrogenation of carbon-carbon double bonds (e.g. see O. Albers et. al. in *J. Organomet. Chem*, 1984, C62, 272; Ohta T. et al. in *J. Org. Chem.*, 1987, 52, 3174-3176; Noyori R. et al. in *J. Am. Chem. Soc.*, 1986, 108, 7117-7119; or Takaya H. et al. in *Am. Chem. Soc.*, 1987, 109, 1596-1597).

Despite their usefulness, only indirect syntheses (i.e. more than one step) of said [Ru(diene)(OOCR)$_2$]$_n$ from [(diene) RuCl$_2$]$_n$ (which is one of the most common commercially available starting materials) are described in the literature. Indeed, the reported preparations of [Ru(diene)(OOCR)$_2$]$_n$ require complexes of the type [(diene)Ru(methylallyl)$_2$] as intermediates, as shown in the following scheme:

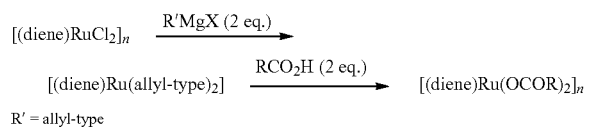

In this way, the preparation of some complexes of type [(diene)Ru(OOCR)$_2$]$_n$, wherein diene is COD or NBD, and R is CF$_3$, CCl$_3$, CHCl$_2$, CH$_3$ or some aryl, have been described (see H. Doucet et. al., *Tetrahedron Asymmetry*, 1996, 7, 525-528; B. Heiser et. al., *Tetrahedron Asymmetry*, 1991, 2(1), 51-62; M. O. Albers et al., *Inorganic Syntheses*, 1989, 26, 249-58; or M. O. Albers et. al. *J. Organomet. Chem*, 1984, C62, 272).

The synthetic pathway described in those publications suffers from the following major drawbacks:
the synthesis of the allyl intermediates, such as [(diene)Ru (bismethylallyl)$_2$], obtained from [Ru(diene)Cl$_2$]$_n$ is very diluted, requires the use of a Grignard reagent and intermediates obtained are only mildly stable, in both solution and solid state, thus complicating an industrial implementation of such synthetic operations;
the preparation of [Ru(diene)(OOCR)$_2$], with the prior art method requires at least two steps starting from [Ru(diene)Cl$_2$], and requires the formation of an intermediate difficult to handle;
methylallyl ligand displacement by protonation is shown only using halo acetic acids or some aryl carboxylic acids, i.e this method is not general;
[(COD)Ru(acetate)$_2$] could not be obtained directly from the bis-methylallyl complex and had been synthesized from [(COD)Ru(OOCCF$_3$)$_2$]$_2$ by anionic ligand exchange with acetate salts, adding thus an additional step to the overall process. Moreover the overall yield of its preparation is quite poor.

Furthermore the known [(diene)Ru(OOCR)$_2$]$_n$ compounds (cited above) suffer from drawbacks of also being only mildly stable in the presence of air, rendering thus the manipulation of the starting materials, as well as the preparation of the [Ru(PP)(OOCR)$_2$] catalysts, difficult and time consuming.

B. Kavanagh et al. (in *J. Chem. Soc. Dalton Trans.* 1993, 328) reports the preparation of Ru(IV)-dicarboxylate complexes from dimeric Ru(IV) which is a much more reactive species than the polymeric [(diene)Ru(Cl)$_2$]. Furthermore, the chemistry of Ru(IV) is quite different from that of Ru(II), not only because of the different oxidation state (Ru(IV) being labile and Ru(II) being inert) but also because of the presence of different ligands (allylic anion versus a carbon carbon π system), and therefore said document cannot suggest the present invention.

Therefore there is a need for an improved process for obtaining complexes of type [(diene)Ru(OOCR)$_2$]$_n$, allowing an improved efficiency. Furthermore, there is also a need for new complexes of type [(diene)Ru(OOCR)$_2$]$_n$, allowing a simpler manipulation, while ensuring high yield for the production of [Ru(PP)(OOCR)$_2$] catalysts, for instance.

DESCRIPTION OF THE INVENTION

We have now surprisingly found that the complexes [(diene)Ru(OOCR)$_2$]$_n$ can be directly obtained, in one step, from the precursor [Ru(diene)Cl$_2$] by reacting said precursor with a carboxylic acid salt under convenient and highly productive reaction conditions.

In order to overcome the problems aforementioned, the present invention relates to a process for the preparation of a compound of formula

wherein
n is 1 or 2;
v is 0, 1 or 2;
S is a coordinated molecule of a polar aprotic solvent or water;
"diene" represents a linear or branched C$_4$-C$_{15}$ hydrocarbon compound comprising two carbon-carbon double bonds or a cyclic C$_7$-C$_{20}$ hydrocarbon group comprising two carbon-carbon double bonds; and
R$^1$ represents:
a hydrogen atom;
a pyridyl group;
a phenyl group optionally substituted by one to five halogen atoms and/or C$_{1-4}$ alkyl or alkoxyl groups; or
a C$_{1-18}$ alkyl or alkenyl group which is
optionally halogenated;
optionally substituted by one phenyl group, the phenyl group being optionally substituted by one to five halogen atoms and/or by C$_{1-4}$ alkyl or alkoxyl groups; and
optionally comprising one or two OH, amino, ether or thioether functional groups;
comprising the step of reacting a precursor compound of formula

wherein "diene" has the same meaning as defined in formula (I);

in the presence of a carboxylate $(R^1COO)_mM$, wherein $R^1$ is as defined above and M is an alkaline (m is 1) or alkaline earth (m is 2) cation, and said reaction is carried out in a polar aprotic solvent and under inert atmosphere.

For the sake of clarity, it has to be mentioned that compound (I) comprises complexes having various structures, that is to say monomers wherein each $R^1COO$ group is coordinated to only one Ru (i.e. [(diene)Ru(OOCR$^1$)$_2$]), or dimers wherein at least one of the $R^1COO$ group is coordinated to two Ru (e.g. [(diene)Ru(OOCR$^1$)(μ-OOCR$^1$)]$_2$ or [((diene)Ru(μ-OOCR$^1$)$_2$]$_2$).

For the sake of clarity, it has to be mentioned that by the expression "hydrocarbon compound comprising two carbon-carbon double bonds", used in the definition of diene, it is meant a neutral ligand and not an allylic system.

According to a particular embodiment of the invention, said S is the same as the polar aprotic solvent used as process solvent or is water. The latter being, e.g., present in the reaction mixture during the process. According to a particular embodiment of the invention, said S is an amine or an amide, for example the one used as polar aprotic solvent such as one described herein below. According to a particular embodiment of the invention, said compound (I) is a compound wherein v is 0, i.e. a compound of formula [(diene)Ru(OOCR$^1$)$_2$]$_n$.

According to a particular embodiment of the invention, said "diene" is a $C_7$-$C_{12}$, or a $C_7$-$C_{10}$, hydrocarbon compound comprising two carbon-carbon double bonds, optionally substituted, e.g. a cyclic $C_7$-$C_{12}$, or a $C_7$-$C_{10}$, hydrocarbon compound comprising two carbon-carbon double bonds. As well understood by a person skilled in the art, by "cyclic hydrocarbon" it is understood a compound comprising a cyclic moiety.

As non-limiting examples of suitable "diene" one may cite compounds such as COD (cycloocta-1,5-diene) or NBD (norbornadiene), 2,4-dimethyl-1,3-pentadiene or yet cyclohepta-1,4-diene.

The examples of "diene" provided above are applicable for both compounds (I) and (II).

The precursor (II) is well known from the literature, and in particular [(COD)Ru(Cl)$_2$] or [(NBD)Ru(Cl)$_2$].

Another constituent of compound (I) is the carboxylic group $R^1COO$. The compounds of formula (I) can be monomeric (n=1), or dimeric (n=2) depending mainly on the exact nature of the group $R^1$, e.g. when $R^1$ is a methyl group the compound is monomeric, while when $R^1$ is $CCl_3$ the compound is dimeric. In some cases, said compound (I) may exist in the two forms (monomeric and dimeric).

According to a particular embodiment of the invention, said $R^1$ group represents:
  a $C_{1-12}$ alkyl group which is
    optionally halogenated;
    optionally substituted by one phenyl group; and
    optionally comprising one OH, amino or ether functional group; or
  a phenyl group optionally substituted by one to three, or five, halogen atoms and/or by $C_{1-4}$ alkyl or alkoxyl groups.

According to a particular embodiment of the invention, said $R^1$ group represents a $C_{2-10}$ alkyl group, optionally branched in the α and/or β position.

According to a particular embodiment of the invention, said $R^1$ group represents a branched $C_{2-10}$ alkyl group comprising in the α position a tertiary or quaternary carbon atom and/or in the β position a quaternary carbon atom and said $R^1$ optionally comprising one OH, amino or ether functional group, and also optionally comprising one phenyl group, the phenyl group being optionally substituted by one to five halogen atoms and/or by $C_{1-4}$ alkyl or alkoxyl groups.

For the sake of clarity, by the expression "α position" it is meant the usual meaning in the art, i.e. the carbon atom directly bound to the COO moiety of the group $R^1COO$. Similarly by the expression "β position" it is meant a carbon atom directly bound to the α position.

The $R^1COO$ group of compound (I) is introduced by reacting the compound $(R^1COO)_mM$ with compound (II). According to a particular embodiment of the invention, said M cation is $Na^+$, $K^+$, $Mg^{2+}$, $Ca^{2+}$ or $Ba^{2+}$, and in particular $Na^+$ or $K^+$.

As non-limiting examples of suitable $R^1COOM$, and consequently of the $R^1COO$ group of (I), one may cite the potassium or sodium salts of acetate, mono-, di-, tri-chloroacetate, propionate, isobutyrate, pivalate, $^t$Bu-acetate, 2-Et-hexanoate, cyclohexanecarboxylate, picolinate, cinnamate, benzoate, 4-Me-benzoate, 4-OMe-bentoate, 3,5-dichloro-benzoate, isovalerate, adamantate or sec-butyrate.

Said $R^1COOM$ can be used as a preformed salt or can be generated in situ. Indeed, $R^1COOM$ can be formed in situ by adding to the reaction medium a base (such as an amine, an alkaline or alkaline-earth hydroxide or alkoxide, or alkaline carbonates) and then an acid $R^1COOH$, or vice versa.

As well understood by a person skilled in the art, by "polar aprotic solvent" it is understood that said solvent has a $pK_a$ above 18 and a dielectric constant $\in$ above 20, said constant being measured at standard conditions. Said constant can be retrieved in chemical Handbooks such as "Handbook of Chemistry and Physics", 87$^{th}$ edition, 2006-2007, page 15-13 to 15-23, ISBN 978-0-8493-0487-3, or such as March's "Advanced Organic Chemistry" 5$^{th}$ edition, ISBN 0-471-58589-0, or any other similar reference.

According to a particular embodiment of the invention, said solvent has a $pK_a$ above 20 and a dielectric constant $\in$ above 30, said constant being measured at standard conditions. Of course, a person skilled in the art knows that the choice of the solvent is a function of the nature of the complex and the person skilled in the art is well able to select the solvent most convenient in each case to optimize the reaction.

It is also well understood by the person skilled in the art that said solvent is a liquid with a melting point below the reaction temperature. It is also useful to mention that another invention's process advantage is that the solvent used does not need particular requirements concerning the water contents, e.g. does not need to be anhydrous, fact that simplifies significantly any industrialization of said process. In particular, technical grade solvents can be used, e.g. which may contain up to 1 or 2% w/w water.

As typical example of said solvent, one may cite the following ones:
  a $C_{2-12}$ amide, in particular a $C_{3-8}$ N-alkyl or N,N-dialkyl amide (e.g. acetamide, N,N-dimethyl-acetamide, N,N-dimethyl-formamide, N-acetyl piperidine or N-acetylpyrrolidine),
  a $C_{2-6}$ sulphoxide (e.g. DMSO),
  a $C_{6-9}$ N-alkyl lactame (e.g. N-methyl pyrrolidone),
  a $C_{4-8}$ carbamate or urea (e.g. tetramethylurea),
  a $C_{4-8}$ amine (e.g. $^t$Bu-amine) or
  mixture thereof.

Particularly appreciated solvents are $C_{3-8}$ N,N-dialkyl amides (N,N-dimethyl-formamide or N,N-dimethyl-acetamide), $C_{5-10}$ lactams (N-methylpyrrolidone) or $^t$Bu-amine.

The process of the invention as mentioned can be carried out in a broad range of temperature. According to a particular embodiment of the invention, the temperature is comprised between 10° C. and 100° C., more preferably between 15° C. and 70° C. Of course, a person skilled in the art is also able to select the preferred temperature as a function of the melting and boiling point as well as of the specific properties of said solvent as well as the desired time of reaction or conversion.

The process of the invention as mentioned is carried out under an inert, or an essentially oxygen free atmosphere. A person skilled in the art knows what is meant by an inert atmosphere, and as non-limiting examples of such atmosphere, one may cite a nitrogen or argon atmosphere.

Typical manners to execute the invention's process are reported herein below in the examples.

Some of the complexes of formula (I) obtained by the invention's process are new compounds possessing very interesting properties. Therefore, another object of the present invention concerns the compounds of formula $$\{[(diene)Ru(OOCR^2)_2]_n(S)_v\} \quad (I')$$

wherein n, v, S and "diene" have the meaning indicated above for compound (I); and $R^2$ represents

- a branched $C_{2-18}$ alkyl group comprising in the a position a tertiary or quaternary carbon atom and/or in the $\beta$ position a quaternary carbon atom; said group optionally comprising a OH, amino or ether functional group; said group being optionally substituted by a one phenyl group, the phenyl group being optionally substituted by one to five halogen atoms and/or by $C_{1-4}$ alkyl or alkoxyl groups; or
- a $CHR^3Ph$ group, wherein $R^3$ is a OH or $NH_2$ group and Ph is a phenyl group optionally substituted by one to five halogen atoms and/or by $C_{1-4}$ alkyl or alkoxyl groups.

Said complexes of formula (I') proved to be particularly stable to the air and suitable for a simplified preparation of the known catalysts of formula $[Ru(PP)(OOCR)_2]$, as will be shown further below.

According to a particular embodiment of the compound (I'), said compounds are those wherein diene represents COD or NBD.

According to a particular embodiment of the compound (I'), said $R^2$ group is:

- a branched $C_{3-10}$ alkyl group of formula $C(R^4)_2C(R^5)_3$, wherein each $R^4$ or $R^5$, independently from each other, represents a hydrogen atom or a $C_{1-3}$ alkyl group, provided that if all $R^4$ are hydrogen atoms then all $R^5$ are alkyl groups, or if at least one $R^5$ is a hydrogen atom then at least one $R^4$ is an alkyl group; said $R^2$ optionally comprising a OH, amino or ether functional group; or
- a $CR^7R^6Ph$ group, wherein $R^6$ is a methyl group or OH or $NH_2$ group, $R^7$ is a methyl group or a hydrogen atom, and Ph is a phenyl group optionally substituted by one to five halogen atoms and/or by $C_{1-4}$ alkyl or alkoxyl groups.

According to a particular embodiment of the compound (I'), said $R^2$ group represent a branched $C_{3-10}$ alkyl group, or even a branched $C_4$ alkyl group, as above defined.

For the sake of clarity, it is noted that the carbon atom bearing the $R^3$ groups is the $\alpha$ position of said $R^2$, and similarly the carbon atom bearing the $R^4$ groups is the $\beta$ position of said $R^2$.

According to a particular embodiment of the compound (I'), $R^2$ represents a $^tBu$, $^iPr$, neopentyl, $^{sec}Bu$ or adamantly group.

According to a particular embodiment of the compound (I'), v is 0. Alternatively v can be 1 or 2, in particular when the invention's process is carried out in a solvent such as polar aprotic amide or amine (in such a case S would be the same amine or amide, for example as defined herein above.

According to a particular embodiment of the compound (I'), is one of the following one: $\{[(COD)Ru(O_2C^tBu)]_2(\mu$-$O_2C^tBu)_2\}$, $[(COD)Ru(O_2C^tBu)_2]$, $\{[(NBD)Ru(O_2C^tBu)]_2(\mu$-$O_2C^tBu)_2\}$, $[(NBD)Ru(O_2C^tBu)_2]$, $\{[(COD)Ru(O_2C^iPr)]_2(\mu$-$O_2C^iPr)_2\}$, $[(COD)Ru(O_2C^iPr)_2]$, $\{[(COD)Ru(O_2CCH_2{}^tBu)]_2(\mu$-$O_2CCH_2{}^tBu)_2\}$, $[(COD)Ru(O_2CCH_2{}^tBu)_2]$, $\{[(COD)Ru(O_2CAd)]_2(\mu$-$O_2CAd)_2\}$ (Ad meaning adamantly), $\{[(COD)Ru(O_2C^{sec}Bu)]_2(\mu$-$O_2C^{sec}Bu)_2\}$, $[(COD)Ru(O_2C^{sec}Bu)_2]$, $[(COD)Ru(O_2CC(Me)_2NH_2)_2]$, $[(COD)Ru(O_2CC(Me)_2OH)_2]$, $[(COD)Ru(O_2CC(Me)_2OMe)_2]$, $[(COD)Ru(O_2CCH(OH)Ph)_2]$, $[(COD)Ru(O_2CC(Me)_2CH_2OH)_2]$, or $\{[(COD)Ru(O_2CC(Me)_2CH_2OH)]_2(\mu$-$O_2CC(Me)_2CH_2OH)_2\}$.

As mentioned above, one of the aims of the present invention is also to provide complexes of type $[(diene)Ru(OOCR)_2]_n$, allowing a simpler manipulation, while ensuring high yields for the production of $[Ru(PP)(OOCR)_2]$ catalyst, and the corresponding process for the preparation of said $[Ru(PP)(OOCR)_2]$ catalyst.

Therefore another object of the present invention concerns a process for the preparation of a compound of formula $$[Ru(PP)(OOCR^2)_2] \quad (III)$$

wherein PP represents a $C_{25-60}$ bis(diarylphosphine) and $R^2$ a group as defined above for compound (I');
said process being characterised in that a complex of formula $$\{[(diene)Ru(OOCR^2)_2]_n(S)_v\} \quad (I')$$

as defined above;
is reacted with a $C_{25-60}$ bis(diarylphosphine) (PP), at a temperature comprised between 20° C. and 200° C.

The advantage of said process is that it can be carried out, with very efficient results, also under an oxygen containing atmosphere, such as air (i.e. without any particular technical requirement), since the new starting materials are themselves stable under such conditions, to the contrary of the prior art starting materials.

The bis(diarylphosphine) (PP) are known to be air-stable per se and are also well known by a person skilled in the art. As typical, non-limiting, examples one may cite the following ones: bis(diphenylphosphino)methane, 1,2-bis(diphenylphosphino)ethane, cis-1,2-bis(diphenylphosphino)ethylene, 1,2-bis(diphenyl phosphino)benzene 1,3-bis(diphenylphosphino)propane, 1,2-bis(diphenylphosphino) propane (PROPHOS, R or S enantiomer), 1,4.bis(diphenylphosphino) butane, 9,9-dimethyl-4,5-bis(diphenylphosphino)xanthene (Xantphos), 4,6-bis(diphenylphosphino)phenoxazine (Nixantphos) 2,2'-bis(diphenylphosphino)-1,1'-binaphthyl (BINAP, racemic or R or S enantiomer), 2,2'-bis(diphenylphosphino)-1,1'-biphenyl (BIPHEP, racemic or R or S enantiomer), 5,5'-Bis(diphenylphosphino)-4,4'-bi-1,3-benzodioxole (SEGPHOS, racemic or R or S enantiomer).

The process for the preparation of compound (III), is carried out conveniently in a solvent. Said solvent can be any solvent previously used in the prior art for the preparation of $[Ru(PP)(OOCR)_2]$ catalysts in general. The choice of the solvent is a function of the nature of the complex and the person skilled in the art is well able to select the solvent most convenient in each case to optimize the hydrogenation reaction. However as typical example of said inert solvent one may cite solvents such as:

- $C_{6-10}$ aromatic solvents such as toluene, anisole or xylene,
- $C_{3-9}$ esters such as ethyl acetate, isopropyl acetate, butyl acetate,
- $C_{4-20}$ ethers such as diethylether, dibutylether, tetrahydrofurane; or
- the mixtures thereof.

Particularly appreciated solvent are the aromatics, ethers or mixtures thereof.

As mentioned above, the preparation of compound (III) can be carried out under inert or oxygen containing atmosphere. For inert atmosphere it is meant the same as above. For oxygen containing atmosphere it is meant any mixture of an inert atmosphere and oxygen, such as for example air. According to an embodiment of the present invention it is preferable to carry out the process under an oxygen containing atmosphere.

For the sake of clarity, it has to be mentioned that the present complexes (I), (I'), (II) and (III) are formally all Ru(II) complexes.

Typical manners to execute the invention's process are reported herein below in the examples.

EXAMPLES

The invention will now be described in further detail by way of the following examples, wherein the temperatures are indicated in degrees centigrade and the abbreviations have the usual meaning in the art.

All reagents and solvents were used as purchased in technical grade without further purification. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CD_2Cl_2$ unless indicated otherwise. Chemical shifts are listed in ppm, and coupling constant in Hz. IR spectra were recorded on a Perkin Elmer FT-IR spectrometer, and the frequencies are given in $cm^{-1}$.

Example 1

Preparation of Some Complexes of Formula (I) or (I') According to the Invention's Process Synthesis of $\{[(COD)Ru(O_2C^tBu)]_2(\mu-O_2C^tBu)_2\}$ and $[(COD)Ru(O_2C^tBu)_2]$: by Direct Reaction of Polymeric $[(COD)RuCl_2]_n$ with Pivalic Acid in the Presence of a Base, in DMF

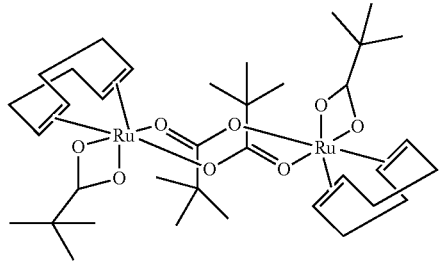

Pyvalic acid (10.0 g, 98 mmol) was added at room temperature to a suspension of $[(COD)RuCl_2]_n$ (10.0 g, 35.6 mmol) in DMF (40 g), under nitrogen. The mixture was heated to 50° C. and then an aqueous KOH solution (45%, 89 mmol) was added dropwise over 1 hour under stirring. The reaction mixture was then stirred at 50° C. for further 20 hours during which the product precipitated out. The mixture was then cooled down to 5° C. and the microcrystalline solid was collected by filtration and the mother liquors set apart. The solid was then washed with DMF (2×50 ml), water (3×50 ml) and then MeOH (50 ml) to afford 12.4 g of the dimeric product (85% yield) after drying under vacuum.

IR (neat): 2953.5 (m), 2950-2920 (w) 1568.1 (s); 1479 (s), 1406 (s).

$^1$H-NMR: 4.5 (m, 1H, CH); 4.3 (m, 1H, CH); 4.2 (m, 1H, CH); 4.0 (m, 1H, CH); 2.5 (m, 2H, $CH_2$); 2.3 (m, 2H, $CH_2$); 2.2 (m, 1H, $CH_2$); 2.1 (m, 1H, $CH_2$); 2.0 (m, 2H, $CH_2$); 1.12 (s, 9H, tBu); 1.11 (s, 9H, tBu).

$^{13}$C-NMR: 194.5 (O—C=O); 191.9 (O—C=O); 97.9 (CH); 96.5 (CH); 88.5 (CH); 83.5 (CH); 41.6 (C); 40.9 (C); 30.3 ($CH_2$); 29.8 ($CH_2$); 28.4 ($CH_2$); 28.2 ($CH_3$); 28.1 ($CH_2$); 27.9 ($CH_3$).

The mother liquors obtained above were concentrated to allow crystallization of $[(COD)Ru(O_2C^tBu)_2]$ which was collected, washed with cold MeOH and dried in vacuo to give 1.7 g of product in the monomeric compound form.

IR (neat): 2959 (m), 2950-2920 (w); 1476 (s), 1492 (s), 1426 (s).

$^1$H-NMR: 4.5 (m, 2H, CH); 3.2 (m, 2H, CH); 2.38 (m, 2H, $CH_2$); 2.3 (m, 2H, $CH_2$); 2.2 (m, 2H, $CH_2$); 2.08 (s, 2H, $CH_2$); 2.0 (m, 2H, $CH_2$); 1.05 (s, 18H, tBu).

$^{13}$C-NMR: 199 (O—C=O); 89.3 (CH); 85.7 (CH); 40.5 (C); 31.6 ($CH_2$); 27.7 ($CH_2$); 26.2 ($CH_3$).

Synthesis of $\{[(COD)Ru(O_2C^tBu)]_2(\mu-O_2C^tBu)_2\}$: by Direct Reaction of Polymeric $[(COD)RuCl_2]_n$ with Pivalic Acid in the Presence of a Base, in NMP Pyvalic acid (6.0 g, 59 mmol) was added at room temperature, under nitrogen, to a suspension of $[(COD)RuCl_2]_n$ (5.0 g, 17.8 mmol) in NMP (20 g). The mixture was heated to 50° C. and then an aqueous KOH solution (45%, 54 mmol) was added dropwise over 1 hour under stirring. The reaction mixture was then stirred at 50° C. for further 20 hours during which the product precipitated out. The mixture was then cooled down to 5° C. and the microcrystalline solid was collected by filtration. The solid was then washed with NMP (2×20 ml), water (3×50 ml) and then MeOH (20 ml) to afford 6.0 g of product (82% yield) after drying under vacuum.

The analytical data where identical to the ones obtained above.

Synthesis of $\{[(COD)Ru(O_2C^tBu)(^tBuNH_2]_2(\mu-O_2C^tBu)_2\}$: by Direct Reaction of Polymeric $[(COD)RuCl_2]_n$ with Pivalic Acid in the Presence of a Base in $tBuNH_2$ Pyvalic acid (6.0 g, 59 mmol) was added at room temperature, under nitrogen, to a suspension of $[(COD)RuCl_2]_n$ (5.0 g, 17.8 mmol) in $tBuNH_2$ (20 g). The mixture was heated to 50° C. and then an aqueous KOH solution (45%, 54 mmol) was added dropwise over 1 hour under stirring. The reaction mixture was then stirred at 50° C. for further 20 hours during which the product precipitated out. The mixture was then cooled down to 5° C. and the microcrystalline solid was collected by filtration. The solid was then washed with water (3×50 ml) and then with cold MeOH (20 ml) to afford 6.4 g of product (74% yield) after drying under vacuum.

IR (neat)ν: 3927.9 (w), 2957 (m), 2950-2920 (w) 1578.5 (s); 1560.6 (s), 1488 (s), 1478.4 (s), 1438 (s).

$^1$H-NMR: 9.1 (bd, 1H, J=9.9, $NH_2$); 4.2 (m, 1H, CH); 3.97 (m, 1H, CH); 3.72 (m, 1H, CH); 3.37 (m, 1H, CH); 2.75 (bd, 1H, J=9.9, $NH_2$); 2.4-2.0 (series of m, 6H, $CH_2$); 1.8 (m, 2H, $CH_2$); 1.32 (s, 9H, tBu); 1.2 (s, 9H, tBu); 1.03 (s, 9H, tBu).

$^{13}$C-NMR: 197.2 (O—C=O); 189 (O—C=O); 89.2 (CH); 89.0 (CH); 81.8 (CH); 77.9 (CH); 54.6 (C); 40.2 (C); 40.15 (C); 30.9 ($CH_2$); 29.9 ($CH_3$); 29.6 ($CH_3$); 28.3 ($CH_3$); 28.2 ($CH_2$); 27.4 ($CH_2$); 26.7 ($CH_3$).

Synthesis of {[(NBD)Ru(O$_2$C$^t$Bu)]$_2$(μ-O$_2$C$^t$Bu)$_2$}: by Direct Reaction of Polymeric [(NBD)RuCl$_2$]$_n$ with Pyvalic Acid in the Presence of Base

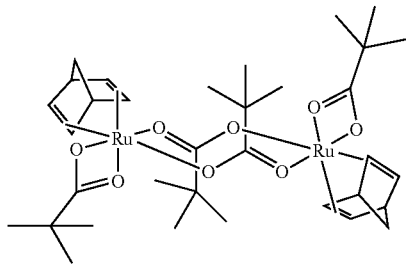

Pyvalic acid (4.6 g, 45 mmol) was added at room temperature to a suspension of [(NBD)RuCl$_2$]$_n$ (4.0 g, 15 mmol) in DMF (15 g), under nitrogen. The mixture was heated to 40° C. and then an aqueous KOH solution (45%, 45 mmol) was added dropwise over 15 minutes under stirring. The reaction mixture was then stirred at 40° C. for further 40 hours during which product precipitate out. The mixture was then cooled down to 5° C. and the solid was collected by filtration. The solid was then washed with DMF (20 ml), water (2×20 ml) and then MeOH (3×10 ml) to afford 5.0 g of product (84% yield) after drying under vacuum.

$^1$H-NMR: 4.8 (m, 1H, CH); 4.6 (m, 1H, CH); 4.4 (m, 2H, CH); 4.0 (broad s, 1H, CH); 3.8 (broad s, 1H, CH); 1.65 (m, 1H, CH$_2$); 1.58 (m, 1H, CH$_2$); 1.12 (s, 9H, tBu); 1.10 (s, 9H, tBu).

$^{13}$C-NMR: 194.7 (O—C=O); 191.2 (O—C=O); 81.8 (CH); 81.3 (CH); 73.7 (CH); 70.7 (CH); 60.2 (CH$_2$); 51.6 (CH); 51.3 (CH); 41.6 (C); 40.7 (C); 28.3 (CH$_3$); 27.9 (CH$_3$).

Synthesis of [(COD)Ru(O$_2$CCH$_2^t$Bu)$_2$] by Direct Reaction of Polymeric [(COD)RuCl$_2$]$_n$ with t-butylacetic Acid in the Presence of a Base

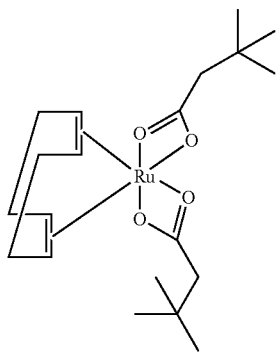

t-Butylacetic acid (12.4 g, 107 mmol) was added at room temperature, under nitrogen, to a suspension of [(COD)RuCl$_2$], (10.0 g, 35.6 mmol) in DMF (40 g). This stirred mixture was then heated to 40° C. and an aqueous KOH solution (45%, 107 mmol) was added dropwise over 1 hour under stirring. The reaction mixture was then stirred at 40° C. for further 20 hours during which a solid precipitates out. The reaction medium was cooled down to room temperature and the precipitate was collected by filtration. The solid was washed with water (3×50 ml), MeOH (50 ml) and dried under vacuum to afford 12.0 g of product (77% yield). Although the product precipitated as a dimer according its IR spectrum, it easily gave the monomer in solution as showed by its NMR spectrum.

IR (neat); 3000-2800 (w); 1575 (s), 1399 (s).

$^1$H-NMR: 4.5 (m, 2H, CH); 3.2 (m, 2H, CH); 2.38 (m, 2H, CH$_2$); 2.3 (m, 2H, CH$_2$); 2.2 (m, 2H, CH$_2$); 2.08 (s, 2H, CH$_2$); 2.0 (m, 2H, CH$_2$); 1.05 (s, 18H, tBu).

$^{13}$C-NMR: 192.8 (O—C=O); 89.3 (CH); 84.5 (CH); 51.6 (CH$_2$); 31.7 (CH$_2$); 31.2 (C); 29.9 (CH$_3$); 27.4 (CH$_2$).

The NMR sample CD$_2$Cl$_2$ solution was then evaporated to dryness to give a solid which appeared to be the monomer at the IR analysis.

IR (neat): 2951 (m), 2950-2820 (w); 1502 (s), 1441 (s), 1415 (s).

Synthesis of {[((COD)Ru(O$_2$C$^i$Pr)]$_2$(μ-O$_2$C$^i$Pr)$_2$} by Direct Reaction of Polymeric [(COD)RuCl$_2$]$_n$ with Potassium Isobutyrate

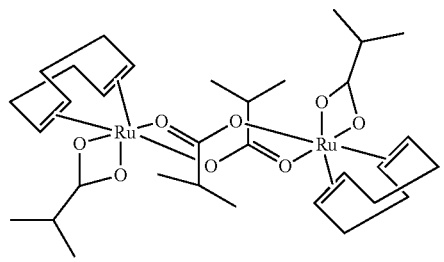

Potassium isobutyrate (13.5 g, 107 mmol) was added at room temperature, under nitrogen, to a suspension of [(COD) RuCl$_2$], (10.0 g, 35.6 mmol) in DMF (30 g). The reaction mixture was stirred at 40° C. for 20 hours during which a solid precipitates. It was then cooled down to room temperature and the precipitate was collected by filtration. The precipitate was washed with water (3×50 ml), MeOH (1×30 ml) and dried under vacuum to afford the product (11.2 g, 82%).

$^1$H-NMR: 4.5 (m, 1H, CH); 4.3 (m, 1H, CH); 4.2 (m, 1H, CH); 4.0 (m, 1H, CH); 2.6-1.9 (series of m, 10H, 2CH+4CH$_2$); 1.11 (d, J=3.2 Hz, 6H, CH$_3$); 1.08 (d, J=3.2 Hz, 6H, CH$_3$).

$^{13}$C-NMR: 193.5 (O—C=O); 191.7 (O—C=O); 97.9 (CH); 97.0 (CH); 88.8 (CH); 84.4 (CH); 39.4 (CH); 38.0 (CH); 30.2 (CH$_2$); 30.1 (CH$_2$); 28.6 (CH$_2$); 28.4 (CH$_2$); 20.2 (CH$_3$); 20.1 (CH$_3$).

Mother liquors were concentrated to allow crystallization of [(COD)Ru(O$_2$C$^i$Pr)$_2$] which was collected, washed with cold MeOH and dried in vacuo to give 1.1 g of product in a monomeric form.

IR (neat): 2950-2820 (w); 1470 (s), 1452 (s), 1426 (s).

Synthesis of [(COD)Ru(O$_2$CPh)$_2$] by Direct Reaction of Polymeric [(COD)RuCl$_2$]$_n$ with Potassium Benzoate in DMA Potassium benzoate (8.5 g, 53.6 mmol) was added at room temperature, under nitrogen, to a suspension of [(COD) RuCl$_2$]$_n$ (5.0 g, 17.8 mmol) in DMA (40 g). This stirred mixture was then heated to 80° C. over 2 hour under stirring. The reaction medium was cooled down to room temperature and water (50 ml) was added. A solid precipitated which was collected washed with water (3×50 ml), cold MeOH (20 ml) and dried under vacuum to afford 7.5 g of product (93% yield).

$^1$H-NMR: 8.1 (d, 4H, Ar); 7.6 (t, 2H, Ar); 7.4 (t, 4H, Ar); 4.8 (m, 2H, CH); 3.3 (m, 2H, CH); 2.5 (m, 4H, CH$_2$); 2.3 (m, 2H, CH$_2$); 2.1 (m, 2H, CH$_2$).

$^{13}$C-NMR: 185 (O—C=O); 131.8 (CH); 131.4 (C); 128.7 (CH); 128.6 (CH); 89.5 (CH); 85.0 (CH); 33.2 (CH$_2$); 28.0 (CH$_2$).

Synthesis of {[(COD)Ru(O$_2$CCl$_3$)$_2$]$_2$(H$_2$O)} by Direct Reaction of Polymeric [(COD)RuCl$_2$]$_n$ with CCl$_3$COOH in the Presence of a Base Trichloroacetic acid (16.0 g, 98 mmol) was added, under nitrogen, at room temperature to a suspension of [(COD)RuCl$_2$]$_n$ (10.0 g, 35.6 mmol) in DMF (40 g). The mixture was heated to 50° C. and then an aqueous KOH solution (45%, 89 mmol) was added dropwise over 1 hour under stirring. The reaction mixture was then stirred at 50° C. for further 20 hours during which the product precipitated out. The mixture was then cooled down to 5° C. and the solid was collected by filtration. The solid was then washed with DMF (2×50 ml), water (3×50 ml) and then MeOH (50 ml) to afford 18.4 g of product (94% yield) after drying under vacuum.

IR (neat): 3350 (b) (H$_2$O); 2950-2920 (w) (COD); 1670 (s) (COO).

$^1$H-NMR: 13.0 (s, 2H, H$_2$O); 4.4-4.2 (broad m, 8H, CH); 2.4-1.8 (broad m, 16H, CH$_2$).

Synthesis of [(COD)Ru(O$_2$CCH$_2$Py)$_2$] by Direct Reaction of Polymeric [(COD)RuCl$_2$]$_n$ with Picolinic Acid in the Presence of a Base

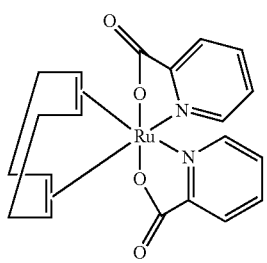

Picolinic acid (13.2 g, 107 mmol) was added. At room temperature, under nitrogen, to a suspension of [(COD)RuCl$_2$]$_n$ (10.0 g, 35.6 mmol) in DMF (40 g). The mixture was heated to 40° C. and an aqueous KOH solution (45%, 107 mmol) was added dropwise during 1 hour under stirring. The reaction mixture was stirred at 40° C. for further 20 hours during which a solid precipitates. The reaction mixture was cooled down to room temperature and the precipitate was collected by filtration. The precipitate was washed with water (3×50 ml), MeOH (50 ml) and dried under vacuum to afford 13.0 g of product (81% yield).

$^1$H-NMR: 8.7 (m, 2H, Ar); 8.0 (m, 2H, Ar); 7.8 (m, 2H, Ar); 7.5 (m, 2H, Ar); 4.5 (m, 2H, CH); 3.3 (m, 2H, CH); 2.8 (m, 2H, CH$_2$); 2.45 (m, 2H, CH$_2$); 2.36 (m, 2H, CH$_2$); 2.2 (m, 2H, CH$_2$).

$^{13}$C-NMR: 172.8 (O—C=O); 151.1 (C—Ar); 148.4 (CH—Ar); 138.0 (CH—Ar); 128.2 (CH—Ar); 127.0 (CH—Ar); 96.6 (CH); 95.7 (CH); 30.9 (CH$_2$); 28.8 (CH$_2$).

Synthesis of [(COD)Ru(O$_2$CCH=CHPh)$_2$]: by Direct Reaction of Polymeric [(COD)RuCl$_2$]$_n$ with Cinnamic Acid in the Presence of a Base

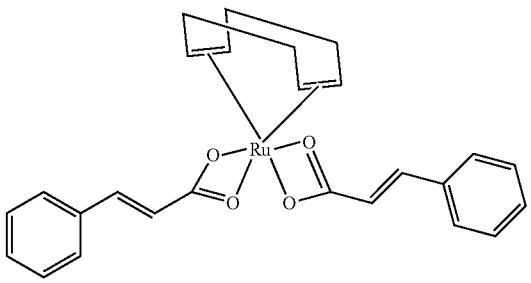

Cinnamic acid (15.8 g, 107 mmol) was added at room temperature, under nitrogen, to a suspension of [(COD)RuCl$_2$]$_n$ (10.0 g, 35.6 mmol) in DMF (40 g). This mixture was then heated to 40° C. and an aqueous KOH solution (45%, 107 mmol) was added dropwise over 1 hour under stirring. The reaction mixture was stirred at 40° C. for further 20 hours during which a solid precipitates. It was then cooled down to room temperature and the precipitate was collected by filtration. It was washed with water (3×50 ml), MeOH (50 ml) and dried under vacuum to afford 12.8 g of product (71% yield).

$^1$H-NMR: 7.7 (d, J=15.03 Hz, 2H, CH); 7.5 (m, 4H, Ar); 7.4 (m, 6H, Ar); 6.3 (d, J=15.03 Hz, 2H, CH); 4.7 (m, 2H, CH); 3.3 (m, 2H, CH); 2.5-1.9 (series of m, 8H, CH$_2$).

$^{13}$C-NMR: 185.4 (O—C=O); 143.9 (CH); 134.8 (C—Ar); 130.7 (CH—Ar); 129.3 (CH—Ar); 128.5 (CH—Ar); 119.5 (CH); 90.1 (CH); 85.5 (CH); 31.9 (CH$_2$); 27.5 (CH$_2$).

Synthesis of {[(COD)Ru(O$_2$CCF$_3$)$_2$]$_2$(DMF)} by Direct Reaction of Polymeric [(COD)RuCl$_2$]$_n$ with Trifluoroacetic Acid in the Presence of a Base, in DMF Trifluoroacetic acid (11.2 g, 98 mmol) was added at room temperature, under nitrogen, to a suspension of [(COD)RuCl$_2$]$_n$ (10.0 g, 35.6 mmol) in DMF (40 g). The mixture was heated to 50° C. and then an aqueous KOH solution (45%, 89 mmol) was added dropwise over 1 hour under stirring. The reaction mixture was then stirred at 50° C. for further 40 hours during which the product precipitated out. Water was added to the mixture to give a suspension. The solid was collected, washed with DMF (2×50 ml), water (3×50 ml) and then MeOH (50 ml) to afford 11.8 g of product (70% yield) after drying under vacuum.

IR (neat): 3026 (w), 2970-2840 (w) 1698.1 (s); 1656.8 (s); 1634.9 (s).

$^1$H-NMR: 8.6 (s, 1H, DMF); 4.6 (m, 1H, CH); 4.4 (m, 1H, CH); 4.3 (m, 1H, CH); 4.2 (m, 4H, CH); 3.99 (m, 1H, CH); 3.2 (s, 3H, DMF); 3.0 (s, 3H, DMF) 2.5-2.3 (m, 8H, CH$_2$); 2.2 (m, 6H, CH$_2$); 2.0 (m, 2H, CH$_2$).

$^{13}$C-NMR: 171.2 (CHO, DMF); 167.6 (q, J$_{C-F}$=37.9 Hz, COO); 167.7 (q, J$_{C-F}$=35.5 Hz, COO); 114.4 (q, J$_{C-F}$=293 Hz,

CF$_3$); 114.3 (q, J$_{C-F}$=288 Hz, CF$_3$); 94.5 (CH); 93.9 (CH); 92.1 (CH); 91.0 (CH); 89.2 (CH); 89.0 (CH); 88.9 (CH); 38.9 (CH$_3$, DMF); 33.4 (CH$_3$, DMF); 30.8 (CH$_2$); 30.5 (CH$_2$); 30.3 (CH$_2$); 30.2 (CH$_2$); 29.7 (CH$_2$); 29.5 (CH$_2$); 28.2 (CH$_2$); 28.1 (CH$_2$).

$^{19}$F-NMR: −75.9, −76.0.

Synthesis of {[(COD)Ru(O$_2$CCF$_2$CF$_3$)$_2$]$_2$(DMF)} by Direct Reaction of Polymeric [(COD)RuCl$_2$]$_n$ with Pentafluoropropionic Acid in the Presence of a Base, in DMF Pentafluoropropionic acid (16.1 g, 98 mmol) was added at room temperature under nitrogen, to a suspension of [(COD)RuCl$_2$], (10.0 g, 35.6 mmol) in DMF (40 g). The mixture was heated to 50° C. and then an aqueous KOH solution (45%, 89 mmol) was added dropwise over 1 hour under stirring. The reaction mixture was then stirred at 50° C. for further 48 hours during which the product precipitated out. Water was then added to the mixture. The solid was collected, washed with DMF (2×50 ml), water (3×50 ml) and then MeOH (50 ml) to afford 13.6 g of product (67% yield) after drying under vacuum.

IR (neat): 3032 (w), 2970-2840 (w); 1702.7 (s); 1661.8 (s); 1633.5 (s).

$^1$H-NMR: 8.6 (s, 1H, DMF); 4.6 (m, 1H, CH); 4.4 (m, 1H, CH); 4.3 (m, 2H, CH); 4.2 (m, 2H, CH); 4.1 (m, 1H, CH); 3.96 (m, 1H, CH); 3.2 (s, 3H, DMF); 3.0 (s, 3H, DMF) 2.6-2.3 (m, 8H, CH$_2$); 2.2 (m, 6H, CH$_2$); 2.0 (m, 2H, CH$_2$).

$^{13}$C-NMR: 171.2 (CHO, DMF); 167.9 (t, J$_{C-F}$=26.4 Hz, COO); 162 (t, J$_{C-F}$=24.7 Hz, COO); 120.5 (CF$_2$); 117.7 (CF$_2$); 105.6 (CF$_3$); 105.3 (CF$_3$); 94.6 (CH); 93.9 (CH); 92.3 (CH); 91.3 (CH); 89.1 (CH); 88.9 (CH); 88.8 (CH); 88.7 (CH); 38.8 (CH$_3$, DMF); 33.4 (CH$_3$, DMF); 30.8 (CH$_2$); 30.5 (CH$_2$); 30.3 (CH$_2$); 30.2 (CH$_2$); 29.7 (CH$_2$); 29.5 (CH$_2$); 28.2 (CH$_2$); 28.1 (CH$_2$).

$^{19}$F-NMR: −83.3; −120.3, −120.8.

Synthesis of [(COD)Ru(O$_2$CC(Me)$_2$NH$_2$)$_2$] by Direct Reaction of Polymeric [(COD)RuCl$_2$]$_n$ with 2-Aminoisobutyric Acid in the Presence of a Base 2-Aminoisobutyric acid (5.0 g, 48.5 mmol) was added at room temperature under nitrogen, to a suspension of [(COD)RuCl$_2$]$_n$ (5.0 g, 17.8 mmol) in DMF (40 g). The mixture was heated to 50° C. and then an aqueous KOH solution (45%, 44 mmol) was added dropwise over 1 hour under stirring. The reaction mixture was then stirred at 50° C. for further 20 hours during which the product precipitated out. The solid was collected, washed with DMF (2×20 ml), water (3×50 ml) and then MeOH (20 ml) to afford 7.1 g of product (97% yield) after drying under vacuum.

IR (neat) v: 3350-2700 (w); 1608 (s).

$^1$H-NMR(CD$_3$OD): 4.47 (m, 2H, CH); 4.4 (d, J=13.7 Hz, 2H, NH$_2$); 3.78 (d, J=13.7 Hz, 2H, NH$_2$); 3.59 (m, 2H, CH); 2.5-2.1 (m, 8H, CH$_2$); 1.55 (s, 6H, CH$_3$); 1.43 (s, 6H, CH$_3$).

$^{13}$C-NMR: 177.5 (O—C=O); 93.4 (CH); 92.6 (CH); 59.2 (C); 30.3 (CH$_2$); 30.2 (CH$_2$); 29.6 (CH$_3$); 29.5 (CH$_3$).

Synthesis of {[(COD)Ru(O$_2$CAd)]$_2$(µ-O$_2$CAd)$_2$} by Direct Reaction of Polymeric [(COD)RuCl$_2$]$_n$ with Adamantic Acid in Presence of a Base

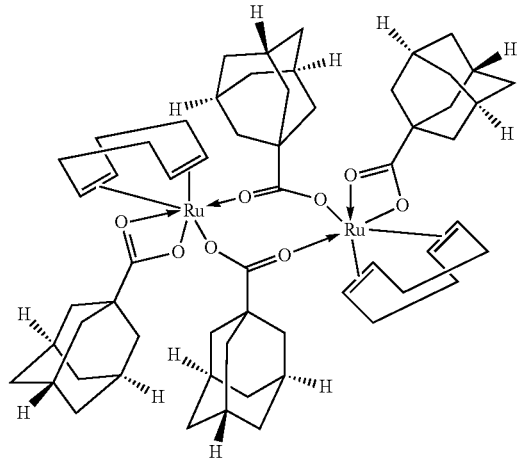

Adamantic acid (177.0 g, 0.982 mol) was added at room temperature to a suspension of [(COD)RuCl$_2$]$_n$ (100.0 g, 0.356 mol) in DMF (800 ml). The mixture was heated to 50° C. and then an aqueous KOH solution (45%, 0.892 mol) was added dropwise for 30 min under stirring. The reaction mixture was then stirred at 50° C. for further 48 hours during which product precipitated out. The mixture was then cooled down to 5° C. and the solid was collected by filtration. It was then washed with DMF (2×500 ml), water (3×500 ml) and then MeOH (500 ml) to afford after drying under vacuum 196 g of product (95% yield).

$^1$H-NMR (CD$_2$Cl$_2$): 4.5 (m, 2H, CH); 4.3 (m, 2H, CH); 4.2 (m, 2H, CH); 4.0 (m, 2H, CH); 2.8-1.2 (series of m, 76H, CH=CH$_2$).

$^{13}$C-NMR (CD$_2$Cl$_2$): 193.4 (O—C=O); 190.9 (O—C=O); 97.8 (CH); 96.5 (CH); 88.3 (CH); 83.3 (CH); 43.7 (C); 42.9 (C); 40.4 (CH); 40.0 (CH); 37.4 (CH); 37.2 (CH); 30.3 (CH$_2$); 29.8 (CH$_2$); 29.2 (CH$_2$); 28.9 (CH$_2$); 28.4 (CH$_2$); 28.2 (CH$_2$).

Synthesis of [(COD)Ru(O$_2$CPhp(OMe))$_2$] by Direct Reaction of Polymeric [(COD)RuCl$_2$]$_n$ with p-methoxy Benzoic Acid in Presence of a Base

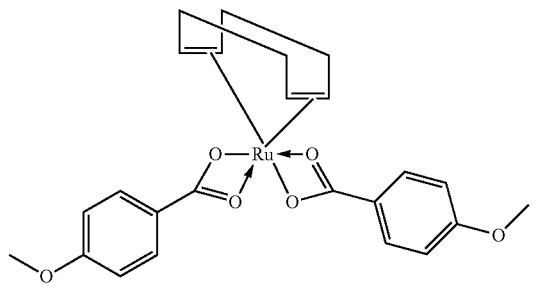

p-Methoxy benzoic acid (16.3 g, 107 mmol) was added at room temperature to a suspension of [(COD)RuCl$_2$]$_n$ (10.0 g, 35.6 mmol) in DMF (40 g). This stirred mixture was then heated to 40° C. and an aqueous KOH solution (45%, 107 mmol) was added dropwise for 1 hour under stirring. The reaction mixture was then stirred at 40° C. for further 20 h during which a bright yellow solid precipitates out. It was cooled down to room temperature and the product was collected by filtration. It was washed with water (3×50 ml), MeOH (50 ml) and dried under vacuum to afford 17.3 g of product n (95% yield).

¹H-NMR (CD₂Cl₂): 8.0 (d, J=9.0 Hz, 4H, Ar); 6.9 (d, J=9.0 Hz, 4H, Ar); 4.8 (m, 2H, CH); 3.8 (s, 3H, CH₃); 3.3 (m, 2H, CH); 2.5 (m, 4H, CH₂); 2.2 (m, 2H, CH₂); 2.0 (m, 2H, CH₂).

¹³C-NMR (CD₂Cl₂): 184.8 (O—C=O); 164.0 (C); 130.8 (CH); 124.4 (C); 113.9 (CH); 90.1 (CH); 85.5 (CH); 55.8 (OCH₃); 31.9 (CH₂); 27.4 (CH₂).

Synthesis of [(COD)Ru(O₂CPho(OMe))₂] by Direct Reaction of Polymeric [(COD)RuCl₂]ₙ with o-Methoxy Benzoic Acid in Presence of a Base

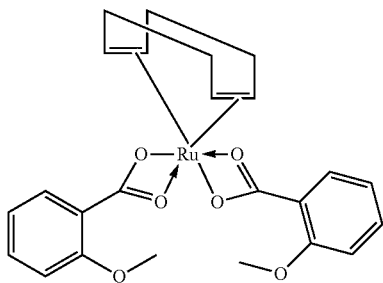

o-Methoxy benzoic acid (16.3 g, 107 mmol) was added at room temperature to a suspension of [(COD)RuCl₂]ₙ (10.0 g, 35.6 mmol) in DMF (40 g). This stirred mixture was then heated to 40° C. and an aqueous KOH solution (45%, 107 mmol) was added dropwise for 1 hour under stirring. The reaction mixture was then stirred at 40° C. for further 20 h during which a bright yellow solid precipitates out. It was cooled down to room temperature and the product was collected by filtration. It was washed with water (3×50 ml), MeOH (50 ml) and dried under vacuum to afford 17.8 g of product n (98% yield).

¹H-NMR (CD₂Cl₂) d 8.0 (m, 2H, Ar); 7.5 (m, 2H, Ar); 7.0 (m, 4H, Ar); 4.8 (m, 2H, CH); 3.9 (s, 3H, CH₃); 3.3 (m, 2H, CH); 2.4 (m, 4H, CH₂); 2.2 (m, 2H, CH₂); 2.1 (m, 2H, CH₂).

¹³C-NMR (CD₂Cl₂) 184.5 (O—C=O); 160.2 (C); 134.3 (CH); 131.9 (CH); 122.5 (C); 120.3 (CH); 112.5 (CH); 90.1 (CH); 85.5 (CH); 56.3 (OCH₃); 31.9 (CH₂); 27.5 (CH₂).

Synthesis of {[(vinylcyclohexene)Ru(tBuCOO)]₂(μ-O₂CtBu)₂} by Direct Reaction of Polymeric [(vinylcyclohexene)RuCl₂]ₙ with Pivalic Acid in Presence of a Base Pivalic acid (2.4 g, 23.5 mmol) was added at room temperature to a suspension of [(vinylcyclohexene)RuCl₂] (2.0 g, 7.1 mmol) in DMF (8 g). This stirred mixture was then heated to 40° C. and an aqueous KOH solution (45%, 21.0 mmol) was added under stirring. The reaction mixture was then stirred at 40° C. for further 20 hours during which a solid precipitates out. It was cooled down to room temperature and the product was collected by filtration. It was washed with water (3×10 ml), MeOH (5 ml); and dried under vacuum to afford 1.8 g of product (61% yield).

¹H-NMR (CD₂Cl₂): 5.0-2.5 (series of m, 8H, CH+CH₂); 2-1.2 (series of m, 16H, CH₂); 1.23 (s, 18H, tBu); 1.09 (s, 18H, tBu).

Example 2

Preparation of Some Complexes of Formula (III) According to the Invention's Process Synthesis of [(dppb)Ru(O₂CᵗBu)₂]: by Reaction of {[(COD)Ru(O₂CᵗBu)]₂(μ-O₂CᵗBu)₂} with DPPB in Xylene Under Nitrogen Xylene (20 ml) was added to the mixture of {[(COD)Ru(O₂CtBu)]₂(μ-O₂CtBu)₂} (5 g, 12 mmol) and 1,4-Bis(diphenylphosphino)butane (DPPB) (5.1 g, 12 mmol) under nitrogen. The reaction mixture was refluxed for 4 h. The solution was cooled down to room temperature, evaporated to dryness and the solid residue was treated with MeOH to give [(dppb)Ru(O₂CtBu)₂] (8.2 g, 11.2 mmol) in 94% yield.

IR (neat)v: 3060-2840 (w); 1495.8 (m); 1480.8 (s); 1424.5 (s).

¹H-NMR: 7.5-7.2 (m, 20H, Ar); 2.43 (m, 4H, CH₂); 1.66 (m, 4H, CH₂); 0.83 (s, 18H, CH₃).

³¹P-NMR: 62.37 (s).

Synthesis of [(dppb)Ru(O₂CᵗBu)₂]: by Reaction of {[(COD)Ru(O₂CᵗBu)]₂(μ-O₂CtBu)₂} with DPPB in Xylene Under Air Not degassed xylene (20 ml) was added to the mixture of {[(COD)Ru(O₂CtBu)]₂ (μ-O₂CtBu)₂} (5 g, 12 mmol) and 1,4-Bis(diphenylphosphino)butane (DPPB) (5.1 g, 12 mmol) under air. The reaction mixture was refluxed for 4 h. The solution was cooled down to room temperature, evaporated to dryness and the solid residue was treated with MeOH to give [(dppb)Ru(O₂CtBu)₂] (8.3 g, 11.2 mmol) in 95% yield.

IR (neat)v: 3060-2840 (w); 1495.8 (m); 1480.8 (s); 1424.5 (s).

¹H-NMR: 7.5-7.2 (m, 20H, Ar); 2.43 (m, 4H, CH₂); 1.66 (m, 4H, CH₂); 0.83 (s, 18H, CH₃).

³¹P-NMR: 62.37 (s).

Synthesis of [(dppb)Ru(O₂CᵗBu)₂]: by Reaction of {[(COD)Ru(O₂CᵗBu)₂] with DPPB in a 3:1 Et₂O/THF Mixture Under Air A 3:1 mixture of not degassed Et₂O/THF (20 ml) was added to the mixture of [(COD)Ru(O₂CtBu)₂] (5 g, 12 mmol) and 1,4-Bis(diphenylphosphino)butane (DPPB) (5.1 g, 12 mmol) under air. The reaction mixture was heated at 40° C. for 20 h. The solution was cooled down to room temperature, evaporated to dryness and the solid residue was treated with MeOH to give [(dppb)Ru(O₂CtBu)₂] (8.0 g, 11.0 mmol) in 92% yield.

The product had the same analytical data as above.

Synthesis of {[(dppb)Ru(O₂CCF₃)₂]₂(H₂O)} by Reaction of {[(COD)Ru(O₂CCF₃)₂]₂(H₂O)}: with DPPB in Et₂O/THF Under Nitrogen A 3:1 mixture of degassed Et₂O/THF (10 ml) was added to the mixture of {[(COD)Ru(O₂CCF₃)₂]₂(H₂O)}: (5 g, 11.3 mmol) and 1,4-Bis(diphenylphosphino)butane (DPPB) (4.8 g, 11.3 mmol) under nitrogen. The reaction mixture was stirred for 16 h at 40° C. The solution was cooled down to room temperature, evaporated to dryness and the solid residue was treated with MeOH to give {[(dppb)Ru(O₂CCF₃)₂]₂(H₂O)} (8.2 g, 10.7 mmol) in 95% yield.

IR (neat): 3060-2840 (w); 1697 (s); 1485.3 (w); 1434.1 (m).

¹H-NMR: 10.6 (s, 2H, H₂O); 7.8-6.9 (m, 40H, Ar); 2.55 (m, 8H, CH₂); 1.77 (m, 8H, CH₂); 0.83 (s, 18H, CH₃).

³¹P-NMR: 51.8 (d, J=50); 51.3 (d, J=50).

Synthesis of {[(dppb)Ru(O₂CCF₃)₂]₂(H₂O)} by Reaction of {[(COD)Ru(O₂CCF₃)₂]₂(H₂O)}: with DPPB in Et₂O/THF Under Air A 3:1 mixture of not degassed Et₂O/THF (10 ml) was added to the mixture of {[(COD)Ru(O₂CCF₃)₂]₂(H₂O)}: (5 g, 11.3 mmol) and 1,4-Bis(diphenylphosphino)butane (DPPB) (4.8 g, 11.3 mmol) under air. The reaction mixture was stirred for 16 h at 40° C.

The solution was cooled down to room temperature, evaporated to dryness and the solid residue was treated with MeOH to give {[(dppb)Ru(O₂CCF₃)₂]₂(H₂O)} (3.9 g, 5.2 mmol) in 45% yield.

IR (neat) v: 3060-2840 (w); 1697 (s); 1485.3 (w); 1434.1 (m).

Synthesis of [(dppb)Ru(O$_2$CPh)$_2$]: by reaction of [(COD)Ru(O$_2$CPh)]$_2$ with DPPB in a 3:1 Et$_2$O/THF Mixture Under Nitrogen A 3:1 mixture of degassed Et$_2$O/THF (20 ml) was added to the mixture of [(COD)Ru(O$_2$CPh)$_2$] (5.0 g, 11.1 mmol) and 1,4-Bis(diphenylphosphino)butane (DPPB) (4.73 g, 11.1 mmol) under air. The reaction mixture was heated at 40° C. for 20 h. The solution was cooled down to room temperature, evaporated to dryness and the solid residue was treated with cold MeOH to give [(dppb)Ru(O$_2$CPh)$_2$] (8.0 g, 10.4 mmol) in 93.7% yield.

IR (neat) v: 3052 (w); 2916 (w); 1497 (m); 1483 (m); 1424 (s); 1375 (s).

Synthesis of [(dppb)Ru(O$_2$CPh)$_2$]: by Reaction of [(COD)Ru(O$_2$CPh)]$_2$ with DPPB in a 3:1 Et$_2$O/THF Mixture Under Air A 3:1 mixture of not degassed Et$_2$O/THF (20 mL) was added to the mixture of [(COD)Ru(O$_2$CPh)$_2$] (5.0 g, 11.1 mmol) and 1,4-Bis(diphenylphosphino)butane (DPPB) (4.73 g, 11.1 mmol) under air. The reaction mixture was heated at 40° C. for 20 h. The solution was cooled down to room temperature, evaporated to dryness and the solid residue was treated with cold MeOH to give [(dppb)Ru(O$_2$CPh)$_2$] (4.9 g, 6.4 mmol) in 58% yield.

IR (neat) v: 3052 (w); 2916 (w); 1497 (m); 1483 (m); 1424 (s); 1375 (s).

$^1$H-NMR: 7.7-7.2 (m, 30H, Ar); 2.6 (broad s, 4H, CH$_2$); 1.87 (broad s, 4H, CH$_2$).

As can be noticed the complexes of formula (I') can be used as precursors of [Ru(PP)(OOCR)$_2$] complexes. Indeed, complexes of formula (I') allow a simplified and highly efficient procedure pour le production of said [Ru(PP)(OOCR)$_2$] complexes, since it can be avoided to work under inert atmosphere, as well as the storage of the staring material does not required any particular precaution to the contrary of the known precursors.

What is claimed is:

1. A compound of formula (I'):

$$\{[(diene)Ru(OOCR^2)_2]_n(S)_v\} \quad (I')$$

wherein
n is 1 or 2;
v is 0, 1 or 2;
S is a coordinated molecule of a polar aprotic solvent or water;
"diene" represents a linear or branched C$_4$-C$_{15}$ hydrocarbon group comprising two carbon-carbon double bonds or a cyclic C$_7$-C$_{20}$ hydrocarbon group comprising two carbon-carbon double bonds; and
R$^2$ represents
a branched C$_{2-18}$ alkyl group comprising in the α position a tertiary or quaternary carbon atom and/or in the β position a quaternary carbon atom; said group optionally comprising a OH, amino or ether functional group; said group being optionally substituted by a one phenyl group, the phenyl group being optionally substituted by one to five halogen atoms and/or by C$_{1-4}$ alkyl or alkoxyl groups; or
a CHR$^3$Ph group, wherein R$^3$ is a OH or NH$_2$ group and Ph is a phenyl group optionally substituted by one to five halogen atoms and/or by C$_{1-4}$ alkyl or alkoxyl groups.

2. The compound according to claim 1, wherein the "diene" is a C$_7$-C$_{12}$ hydrocarbon compound comprising two carbon-carbon double bonds, optionally substituted with a cyclic C$_7$-C$_{12}$ hydrocarbon group comprising two carbon-carbon double bonds.

3. The compound according to claim 1, wherein the polar aprotic solvent is a C$_{2-12}$ amide, a C$_{2-6}$ sulphoxide, a C$_{6-9}$ N-alkyl lactame, a C$_{4-8}$ carbamate or urea, a C$_{4-8}$ amine or a mixture thereof.

4. The compound according to claim 1, wherein v is 0.

5. The compound according to claim 1, wherein the R$^2$ group is:
a branched C$_{3-10}$ alkyl group of formula C(R$^4$)$_2$C(R$^5$)$_3$, wherein each R$^4$ or R$^5$, independently from each other, represents a hydrogen atom or a C$_{1-3}$ alkyl group, provided that if all R$^4$ are hydrogen atoms then all R$^5$ are alkyl groups, or if at least one R$^5$ is a hydrogen atom then at least one R$^4$ is an alkyl group; with R$^2$ optionally comprising a OH, amino or ether functional group; or
a CR$^7$R$^6$Ph group, wherein R$^6$ is a methyl group or OH or NH$_2$ group, R$^7$ is a methyl group or a hydrogen atom, and Ph is a phenyl group optionally substituted by one to five halogen atoms or C$_{1-4}$alkyl or alkoxyl groups.

6. The compound according to claim 5, wherein R$^2$ represents a $^t$Bu, $^i$Pr, neopentyl, $^{sec}$Bu or adamantly group.

7. The compound according to claim 1, wherein the compound is {[(COD)Ru(O$_2$C$^t$Bu)]$_2$(μ$_2$C$^t$Bu)$_2$}, [(COD)Ru(O$_2$C$^t$Bu)$_2$], {[(NBD)Ru(O$_2$C$^t$Bu)]$_2$(μ-O$_2$C$^t$Bu)$_2$}, [(NBD)Ru(O$_2$C$^t$Bu)$_2$], {[(COD)Ru(O$_2$C$^i$Pr)]$_2$(μ-O$_2$C$^i$Pr)$_2$}, [(COD)Ru(O$_2$C$^i$Pr)$_2$], {[(COD)Ru(O$_2$CCH$_2$$^t$Bu)]$_2$(μ-O$_2$CCH$_2$$^t$Bu)$_2$}, [(COD)Ru(O$_2$CCH$_2$$^t$Bu)$_2$], {[(COD)Ru(O$_2$CAd)]$_2$(μ-O$_2$CAd)$_2$}, {[(COD)Ru(O$_2$C$^{sec}$Bu)]$_2$(μ-O$_2$C$^{sec}$Bu)$_2$}, [(COD)Ru(O$_2$C$^{sec}$Bu)$_2$], [(COD)Ru(O$_2$CC(Me)$_2$NH$_2$)$_2$], [(COD)Ru(O$_2$CC(Me)$_2$OH)$_2$], [(COD)Ru(O$_2$CC(Me)$_2$OMe)$_2$], [(COD)Ru(O$_2$CCH(OH)Ph)$_2$], [(COD)Ru(O$_2$CC(Me)$_2$CH$_2$OH)$_2$], or {[(COD)Ru(O$_2$CC(Me)$_2$CH$_2$OH)]$_2$(μ-O$_2$CC(Me)$_2$CH$_2$OH)$_2$}.

8. A process for the preparation of a compound of formula (III)

$$[Ru(PP)(OOCR^2)_2] \quad (III)$$

wherein PP represents a C$_{25-60}$ bis(diarylphosphine) and R$^2$ a group as defined in claim 1;
said process being characterised in that a complex of formula (I')

$$\{[(diene)Ru(OOCR^2)_2]_n(S)_v\} \quad (I')$$

as defined in claim 1;
is reacted with a C$_{25-60}$ bis(diarylphosphine) (PP), at a temperature comprised between 20° C. and 200° C.

* * * * *